(12) United States Patent
Blaine

(10) Patent No.: US 6,572,878 B1
(45) Date of Patent: Jun. 3, 2003

(54) METHOD AND DEVICE FOR TREATING SCARS

(76) Inventor: Robert Blaine, 9624 S. John St., Santa Fe Springs, CA (US) 90670

( * ) Notice: Subject to any disclaimer, the term of this patent is extended or adjusted under 35 U.S.C. 154(b) by 32 days.

(21) Appl. No.: 09/656,852

(22) Filed: Sep. 7, 2000

(51) Int. Cl.[7] .......................... A61F 13/00; A61L 15/00
(52) U.S. Cl. .................. 424/443; 424/402; 424/448; 424/449
(58) Field of Search ................ 424/449, 448, 424/443, 401, 402

(56) References Cited

U.S. PATENT DOCUMENTS

| | | | | |
|---|---|---|---|---|
| 4,728,642 A | * | 3/1988 | Pawelchak et al. | |
| 5,376,117 A | * | 12/1994 | Pinchuk et al. | |
| 5,456,745 A | * | 10/1995 | Roreger et al. | |
| 5,614,201 A | * | 3/1997 | Slavtcheff et al. | |
| 5,976,565 A | * | 11/1999 | Fotinos | |
| 6,270,783 B1 | * | 8/2001 | Slavtcheff et al. | |
| 6,280,765 B1 | * | 8/2001 | Gueret | |
| 6,337,076 B1 | * | 1/2002 | Studin | |

* cited by examiner

*Primary Examiner*—Thurman K. Page
*Assistant Examiner*—Isis Ghali
(74) *Attorney, Agent, or Firm*—McKee, Voorhees & Sease, P.L.C.

(57) ABSTRACT

An improved silicone sheet for preventing or minimizing the appearance of scars impregnated with an antioxidant and/or an antimicrobial. The sheet is preferably self-adhering, and may be applied to an affected area of skin for at least 12 hours per day and for a time period sufficient to either prevent the formation of a scar or minimize the appearance of an existing scar.

5 Claims, No Drawings

METHOD AND DEVICE FOR TREATING SCARS

FIELD OF THE INVENTION

This invention relates to an improved silicone sheet for flattening and fading scars.

BACKGROUND OF THE INVENTION

Scars are marks left on the skin following the healing of a surface injury or wound caused by accidents, disease, or surgery. Scars are composed mainly of the fibrous protein collagen.

The difference between scar tissue and normal skin is the amount of collagen it contains and the way the collagen fibers are arranged. In normal skin, the elongated collagen fibers are well organized mainly in the direction of the crease lines of the skin with only a minor number weaving in the opposite direction. In contrast, the arrangement of collagen fibers in scars is disorganized and distinctly different from the normal tissue surrounding it. As the scar ages, the collagen fibers become more tightly packed and more resistant to removal by the natural enzymes produced by the body.

Many variables can affect the severity of scarring, including the size and depth of the wound, the blood supply to the area, the thickness and color of the skin, and the direction of the scar. The person's age also greatly affects scar formation. For instance, younger skin tends to overheal, resulting in larger, thicker scars in comparison to older skin. Further, the location of the body where the wound occurs will affect the scar's appearance. Generally, scars are more noticeable on tighter, thinner skin.

Hypertrophic and keloid scars are thick, raised scars that are often red and/or darker in color than the surrounding skin, in comparison to the flat, light colored appearance taken on by normal scars as they mature. Keloid scars are thick, puckered, itchy clusters of scar tissue that grow beyond the edges of the wound or incision. Keloids occur when the body continues to produce collagen after a wound has healed. While keloids can appear anywhere on the body, they most commonly appear over the breastbone, on the earlobes, and on the shoulders. Hypertrophic scars differ from keloid scars in that they remain within the boundaries of the original incision or wound. Both keloid and hypertrophic scars can improve over time. However, it is not unusual for them to persist for many years.

Keloid and hypertrophic scars are not only problematic due to their unsightly appearance, but can also cause physcial problems. For instance, if the scar tissue overlays a skeletal joint, it may cause movement of the joint to become painful and restricted. Further, the scars themselves are often accompanied by burning, itching, and pain.

There are currently several methods available for treating and reducing the appearance of keloid and hypertrophic scars. Surgical excision of hypertrophic and keloid scars has proven ineffective in view of the 45–100% rate of scar recurrence. Surgical scar revision involves removing the scarred skin and rejoining the normal skin in a manner such that the wounded area is less noticeable. This scar treatment method is often very expensive, and, as with any surgical procedure, there is always the possibility of surgical complications.

Dermabrasion is used to smooth scar tissue by scraping or shaving off the top layers of the skin using an electric rotary wheel. Dermabrasion is often successful in leveling out the irregularities on surface scars. However, patients usually cannot work for several weeks following the procedure due to pain and discomfort, as well as extreme sensitivity of the skin. Further, several treatments may be required if the scars are deep and extensive.

Another common method of treating scars is through the injection of collagen or fat to fill and elevate depressed scars. While such treatments provide immediate results, the results are not permanent. Thus, continuous retreatments are required. In addition, patients having a personal history of autoimmune diseases, such as rheumatoid arthritis and lupus, cannot safely use collagen treatments.

Other common therapeutic treatments for scars include occlusive dressings, compression therapy, intralesional corticosteroid injections, cryosurgery, radiation therapy, laser therapy, and interferon therapy.

Silicone gel and silicone occulsive sheeting have been widely used in the treatment of hypertrophic and keloid scars. While silicone dressings have proven to be somewhat effective in scar treatment, their occlusive effects are also commonly associated with infection due to the accumulation of microbes on the skin.

There is therefore a need in the art for a method of treating scars which solves the problems of the aforementioned methods.

Accordingly, it is a primary objective of the present invention to provide a device for treating scars which minimizes the appearance of old and new hypertrophic and keloid scars.

It is a further objective of the present invention to provide a device for treating scars which protects the skin and absorbs skin moisture.

It is a further objective of the present invention to provide a device for treating scars which discourages microbial growth.

It is still a further objective of the present invention to provide a device for treating scars which slows free radical reactions on the treated area.

Another objective of the present invention is the provision of an improved silicone sheet for preventing and treating scar tissue.

Another objective of the present invention is the provision of a silicone sheet impregnated with an antioxidant and/or an antimicrobial for scar tissue treatment.

Yet a further objective of the present invention is to provide a device for treating scars which is economical and convenient to use.

The method and means of accomplishing each of the above objectives as well as others will become apparent from the detailed description of the invention which follows hereafter.

SUMMARY OF THE INVENTION

The present invention is an improved silicone sheet for flattening and fading scars. The silicone sheet is impregnated with an antioxidant and/or an antimicrobial. The silicone sheeting serves to prevent the formation of scars and/or flatten and fade the appearance of scars. The antioxidant serves to slow free radical reactions on the skin, thereby promoting skin healing. Further, the antimicrobial helps prevent the accumulation of microbes on the skin often caused by silicone occlusion. The sheet may be designed to self-adhere to the skin, thereby eliminating the need for separate adherents, such as bandages and medical tapes.

DETAILED DESCRIPTION OF THE PREFERRED EMBODIMENT

The present invention relates to an improved silicone sheet for preventing the formation of and treating preexisting scars. While the following disclosure speaks primarily of the invention's use in preventing and treating keloid and hypertrophic scars, the invention is broadly intended for use in the prevention and treatment of all types of scars, including scars caused by burns and acne.

As noted above, silicone has been used in the form of sheets for several years in the management of scars. It has been found that the placement of silicone on the scar tissue in combination with pressure reduces the formation of hypertrophic scar tissue. Silicone offers several advantages over traditional bandages. First, silicone is flexible, therefore allowing the silicone sheets to conform to the contours of the human body. This not only makes the device more comfortable, but helps to prevent the treated area from becoming contaminated. Silicone sheets are also tacky to the touch, thereby allowing it to adhere to the skin.

Any type of silicone gel and/or silicone occlusive sheeting may be used for purposes of this invention. Such substances are well known in the art, and a number of products are available commercially for this purpose, such as Dow Corning Silastic Sheeting (Dow Corning), Cica-Care (Smith & Nephew), Epi-Derm (Biodermis), Nagosil (Nagor), and Nusil Technology. The most preferred silicone gel for use in this invention is Med #6345 manufactured by Nusil Technology due to its high degree of tackiness. The silicone sheeting typically includes a non-adhesive backing to prevent the outside of the device from sticking to clothing, etc.

The silicone portion of this invention is preferably a soft, durable, washable, medical-grade silicone rubber sheet. The thickness of the silicone is not critical, and is primarily limited by convenience and cost. The silicone will typically have a thickness ranging from about 0.5–3.0 mm, with a range of about 0.6–1.5 mm being preferred, and a range of about 1.0–1.2 mm being most preferred. The silicone sheet is preferably semi-occlusive, and preferably has a non-adhesive backing, such as breathable polyurethane film. A release paper made of a non-silicone material, such as polyester, may also be used to cover and protect the silicone prior to application.

The above description of silicone sheets for treatment of scar tissue is well known and not a part of the present invention.

The present invention is directed towards an improved silicone sheet which is impregnated with at least one antioxidant and/or at least one antimicrobial. Applicant has surprisingly discovered that silicone could be combined with either an antioxidant and/or an antimicrobial to form a stable solution. Prior to this invention, it was not realized in the art that an organic oil antioxidant could be effectively combined with a silicone inorganic liquid to form a stable solution for use in treating scars.

Similarly, prior to this invention, it was not understood in the art that silicone could be combined with an antimicrobial to form a stable composition. Instead, it was believed that an antimicrobial, such as benzalkonium chloride, in combination with silicone would result in the formation of an unworkable, tacky solid. The present inventor is the first to realize that silicone can be combined with an antioxidant and/or an antimicrobial to form a stable solution that may be used in the manufacture of a device for treating scars.

Antioxidants are substances capable of inhibiting oxidation. When used in this invention, the antioxidant is useful in preventing fibrosis and decreasing free radical formation. While Vitamin E is the preferred antioxidant for use in this invention, other antioxidants, such as ascorbyl palmitate (L-ascorbic acid), butylated hydroxyanisole, butylated hydroxytoluene, and sodium bisulfite are also suitable.

Preferably, the antioxidant will be used in an amount sufficient to prevent fibrosis and/or decrease radical formation, but not in an amount exceeding the concentration that will go into and remain in solution with the silicone. The amount of antioxidant that may be used in the device of this invention will typically range from about 0.001–10.0% by weight of the sheet, with about 0.01–1.0% by weight being preferred.

In addition or as an alternative to the antioxidant, the silicone may also be impregnated with an antimicrobial. As already explained above, silicone dressings are commonly associated with infection due to the accumulation of microbes on the skin. The silicone sheet of this invention provides the advantage of having an antimicrobial impregnated within. This novel feature prevents the growth of bacterial and other microbes on the skin treatment area.

The antimicrobial for use in this invention is preferably a quaternary ammonium compound. Quaternary ammonium compounds include quaternary morpholium alkyl sulfates, cetylpyridinium chloride, alkyldimethyl benzylammonium chlorides, and alkyltrimethyl ammonium halides. Preferred quaternary ammonium compounds include benzalkonium chloride, octyl decyl dimethyl ammonium chloride, dioctyl dimethyl ammonium chloride, and didecyl dimethyl ammonium chloride. Benzalkonium chloride is the most preferred quaternary ammonium compound.

Other antimicrobials may also be used in this invention so long as they are safe for external use and compatible with the other ingredients in the formulation. Examples of other appropriate antimicrobials for use in this invention include, but are not limited to, acetic acid, ethyl alcohol, chlorhexidine gluconate, ethylene oxide, glutaraldehyde, benzoic acid, hexachlorophene, iodine, isopropyl alcohol, mafenide acetate, methenamine, methenamine mandelate, nitrofurazone, nonoxynol 9, octoxynol 9, selenium sulfide, silver nitrate, silver sulfadiazine, and zinc sulfate.

The silicone should include a disinfecting-effective amount of the antimicrobial. Again, the amount of the antimicrobial that may be used in the device is limited by the amount that will go into and remain in solution with the silicone. This amount will typically range from about 0.001–10.0% by weight of the sheet, with about 0.01–1.0% by weight being preferred.

In manufacturing the device of this invention, the ingredients may be simply combined, molded, and cured to form a sheet. Curing times, temperatures and pressures for forming silicone sheets are standard in the art. The device may include one or more types or grades of silicone which may be combined in order to utilize their mutual benefits. The ingredients may be optionally combined in the presence of a catalyst, such as platinum.

The sheet can be trimmed to the desired shape or size prior to placement on the treatment area. While the silicone is sticky and will self-adhere to the skin, the sheet may also be secured with a lightly conforming bandage or tape. The sheet may preferably include a hypoallergenic adhesive gel border.

In use, the patient should clean the site to be treated and apply the scar treatment silicone sheet with clean hands. The sheet may be optionally trimmed to the size and shape of the area either prior to or after application to the skin. While the sheet is preferably adhesive, it may also be secured with a lightly conforming bandage or tape. The sheet should not be secured to the skin area too tightly, as it may lead to skin irritation. The sheet of this invention should not be used on open wounds or macerations.

For best results, the scar treatment sheet is worn daily, for at least 12 hours per day. The sheet may be worn up to 24 hours per day and reapplied daily for up to 30 days. The treatment site and sheet should be washed with mild soapy water and dried prior to reapplication. The sheet should be used for a length of time sufficient for the patient to observe an improvement in the appearance of the scar. This time period will vary greatly based on the size and severity of the scar, and will generally range from about 72 hours up to about three months or longer. If used for scar prevention, the sheet should be worn daily for at least 12 hours per day for a treatment period for up to about 3 months.

It should be appreciated that minor dosage and formulation modifications of the composition and the ranges expressed herein may be made and still come within the scope and spirit of the present invention.

Having described the invention with reference to particular compositions, theories of effectiveness, and the like, it will be apparent to those of skill in the art that it is not intended that the invention be limited by such illustrative embodiments or mechanisms, and that modifications can be made without departing from the scope or spirit of the invention, as defined by the appended claims. It is intended that all such obvious modifications and variations be included within the scope of the present invention as defined in the appended claims. The claims are meant to cover the claimed components and steps in any sequence which is effective to meet the objectives there intended, unless the context specifically indicates to the contrary.

What is claimed is:

1. A method of minimizing the appearance of scars comprising:

applying a semi-occlusive device to a closed wound on the skin that has or may potentially develop a scar, said device comprising a one layer silicone sheet infused with an antioxidant and an antimicrobial.

2. A method according to claim 1 whereby the device is worn for at least 12 hours per day.

3. A method according to claim 1 whereby the device is applied to the skin daily for at least three days.

4. A method of making a device for minimizing the appearance of scars comprising:

infusing a semi-occlusive, one layer silicone sheet with an antioxidant and an antimicrobial, said silicone sheet being manufactured to include adhesive on one side for application to a closed wound on the skin.

5. A method of minimizing the appearance of scars comprising:

applying a device to a closed wound on the skin that has or may potentially develop a scar, said device comprising a silicone sheet infused with an antioxidant and an antimicrobial.

* * * * *